(12) United States Patent
Halstead et al.

(10) Patent No.: US 9,388,235 B2
(45) Date of Patent: Jul. 12, 2016

(54) METHODS AND COMPOSITIONS FOR THE TREATMENT OF ANTIBODY MEDIATED NEUROPATHIES

(75) Inventors: Susan Halstead, Glasgow (GB); Hugh Willison, Glasgow (GB); Russell P. Rother, Oklahoma City, OK (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 1751 days.

(21) Appl. No.: 12/439,070

(22) PCT Filed: Sep. 5, 2007

(86) PCT No.: PCT/US2007/019416
§ 371 (c)(1),
(2), (4) Date: Dec. 7, 2009

(87) PCT Pub. No.: WO2008/030505
PCT Pub. Date: Mar. 13, 2008

(65) Prior Publication Data
US 2010/0143343 A1    Jun. 10, 2010

Related U.S. Application Data

(60) Provisional application No. 60/842,296, filed on Sep. 5, 2006.

(51) Int. Cl.
*A61K 39/395* (2006.01)
*C07K 16/18* (2006.01)
*A61K 39/00* (2006.01)

(52) U.S. Cl.
CPC ........... *C07K 16/18* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,660,825 | A | 8/1997 | Sims et al. |
| 6,057,131 | A | 5/2000 | Marsh, Jr. et al. |
| 6,100,443 | A | 8/2000 | Sims et al. |
| 6,355,245 | B1 | 3/2002 | Evans et al. |
| 6,515,002 | B2 * | 2/2003 | Illig et al. ............... 514/365 |
| 6,534,058 | B2 | 3/2003 | Fung et al. |
| 2002/0041875 | A1 | 4/2002 | Fung et al. |
| 2003/0129187 | A1 | 7/2003 | Fung et al. |
| 2005/0004031 | A1 | 1/2005 | Subasinghe et al. |
| 2005/0226870 | A1 | 10/2005 | Wang et al. |

FOREIGN PATENT DOCUMENTS

| | | |
|---|---|---|
| EP | 1 739 078 | 1/2007 |
| WO | WO 92/10205 | 6/1992 |
| WO | WO 95/29697 | 11/1995 |
| WO | WO 2004/007553 A1 | 1/2004 |
| WO | WO 2005/002513 | 1/2005 |
| WO | WO 2005/002513 A2 | 1/2005 |
| WO | WO 2007/103134 A2 | 9/2007 |

OTHER PUBLICATIONS

Woodruff et al., Molecul. Immunology, vol. 48, pp. 1631-1642, 2011.*
Kaplan, Curr. Opin. Invest. Drugs, vol. 3, pp. 1017-1023, 2002 (Abstract Only).*
Halstead, S.K. et al., "Complement Inhibition Abrogates Nerve Terminal Injury in Miller Fisher Syndrome," Annals of Neurology, vol. 58(2): 203-210 (2005).
Kaplan, Mariana, "Eculizumab," Current Opinion in Investigational Drugs, vol. 3(7), pp. 1017-1023 (2002).
Tsukamoto and Horiuchi, "Clinical aspects of the complement system," vol. 54(7), pp. 757-762 (2006).
Bird et al., "Single-Chain Antigen-Binding Proteins," Science, vol. 242: 423-426 (1988).
Clackson et al., "Making antibody fragments using phage display libraries," Nature, vol. 352: 624-628 (1991).
Holliger et al., "Diabodies": Small bivalent and bispecific antibody fragments, Proc. Natl. Acad. Sci., vol. 90: 6444-6448 (1993).
Jones et al., "Replacing the complementarity-determining regions in a human antibody with those from a mouse," Nature, vol. 321: 522-525 (1986).
Kabat and Mayers, "Complement and Complement Fixation," Experimental Immunochemistry, Second Edition, pp. 135-139 (1961).
Kohler et al., "Continuous cultures of fused cells secreting antibody of predefined specificity," Nature, vol. 256: 495-497(1975).
Marks et al., "By-passing Immunization Human Antibodies from V-gene Libraries Displayed on Phage," J. Mol. Biol., vol. 222: 581-597 (1991).
Mollnes et al., "Identification of a Human C5 β-Chain Epitope Exposes in the Native Complement Component but Concealed in the SC5b-9 Complex," Scand. J. Immunol., vol. 28: 307-312 (1988).
Montz et al., "Regulation of the Human Autologous T Cell Proliferation by Endogenously Generated C5a," Cellular Immunology, vol. 127: 337-351 (1990).
Müller-Eberhard, Hans J., "Molecular Organization and Function of the Complement System," Ann. Rev. Biochem, vol. 57: 321-347 (1988).
Newman et al., "Primatization" of Recombinant Antibodies for Immunotherapy of Human Diseases: A Macaque/Human Chimeric Antibody Against Human CD4, Biotechnology, vol. 10: 1455-1460 (1992).
Plückthun, A., "Antibodies from *Escherichia coli*," The Pharmacology of Monoclonal Antibodies, vol. 113: 269-315 (1994).
The United States Pharmacopeial Convention, Pharmacopeial Forum, vol. 26(1): 223-227 (2000).

(Continued)

*Primary Examiner* — John Ulm
(74) *Attorney, Agent, or Firm* — Nelson Mullins Riley & Scarborough LLP; Jane E. Remillard, Esq.; Jill Gorny Sloper, Esq.

(57) ABSTRACT

The use of a therapeutic capable of inhibiting complement, e.g., an anti-C5 antibody, to treat antibody mediated neuropathies is disclosed.

16 Claims, 5 Drawing Sheets

(56) References Cited

OTHER PUBLICATIONS

Ward and Zvaifler, "Complement-Derived Leukotactic Factors in Inflammatory Synovial Fluids of Humans," The Journal of Clinical Investigation, vol. 50: 606-616 (1971).
Zapata et al., "Engineering linear F(ab')$_2$ fragments for efficient production in *Escherichia coli* and enhanced antiproliferative activity," Protein Engineering, vol. 8(10): 1057-1062 (1995).
Morgan, B. Paul, "Mechanisms of Tissue Damage by the Membrane Attack Complex of Complement," Complement Inflamm, vol. 6:104-11 (1989).
Fitch et al., "Pharmacology and Biological Efficacy of a Recombinant, Humanized, Single-Chain Antibody C5 Complement Inhibitor in Patients Undergoing Coronary Artery bypass Graft Surgery With Cardiopulmonary Bypass," Circulation, vol. 100(25):, 2499-2506 (1999).
Willison, H.J., The immunobiology of Guillain-Barré syndromes, J. Peripheral Nervous System, vol. 10(2): 94-112 (2005).
Bowes et al., Tolerance to self gangliosides is the major factor restricting the antibody response to lipopolysaccharide core oligosaccharides in Campylobacter jejuni strains associated with Guillain-Barre syndrome, Infect. Immun 70(9):5008-5018 (2002).
Buchwald et al., Immunoglobulin G from a patient with Miller-Fisher syndrome rapidly and reversibly depresses evoked quantal release at the neuromuscular junction of mice, Neurosci. Lett. 201:163-166 (1995).
Bullens et al., Anti-GQ1b antibodies and evoked acetylcholine release at mouse motor endplates, Muscle Nerve 23:1035-1043 (2000).
Bullens et al., Complex gangliosides at the neuromuscular junction are membrane receptors for autoantibodies and botulinum neurotoxin but redundant for normal synaptic function, J. Neurosci. 22(16):6876-6884 (2002).
Chiba et al., Serum anti-GQ1$_b$ IgG antibody is associated with ophthalmoplegia in Miller Fisher syndrome and Guillain-Barre syndrome: clinical and immunohistochemical studies, Neurology 43:1911-1917 (1993).
Fisher, An unusual variant of acute idiopathic polyneuritis (syndrome of ophthalmoplegia, ataxia and areflexia), N. Engl. J. Med. 255(2):57-65 (1956).
Frei et al., Generation of a monoclonal antibody to mouse C5 application in an ELISA assay for detection of anti-C5 antibodies, Mol. Cell. Probes. 1:141-149 (1987).
Goodyear et al., Monoclonal antibodies raised against Guillain-Barre syndrome-associated Campylobacter jejuni lipopolysaccharides react with neuronal gangliosides and paralyze muscle-nerve preparations, J. Clin. Invest 104(6):697-708 (1999).
Hafer-Macko et al., Complement activation in acquired and hereditary amyloid neuropathy, J. Peripher. Nerv. Sys. 5:131-139 (2000).
Hafer-Macko, et al., Immune attack on the Schwann cell surface in acute inflammatory demyelinating polyneuropathy, Ann. Neurol. 39:625-635 (1996).
Halstead et al., Anti-disialoside antibodies kill perisynaptic Schwann cells and damage motor nerve terminals via membrane attack complex in a murine model of neuropathy, Brain 127:2109-2123 (2004).
Halstead et al., Complement inhibition abrogates nerve terminal injury in Miller Fisher syndrome, Ann. Neurol. 58:203-210 (2005).
Hartung, et al., Guillain-Barre syndrome: activated complement components C3a and C5a in CSF, Neurology 37:1006-1009 (1987).
Hill, et al., Recent developments in the understanding and management of paroxysmal nocturnal haemoglobinuria, Br. J. Haematol. 137:181-192 (2007).
Hillmen et al., Effect of eculizumab on hemolysis and transfusion requirements in patients with paroxysmal nocturnal hemoglobinuria, New Eng. J. Med. 350:552-559 (2004).
Hillmen et al., The complement inhibitor eculizumab in paroxysmal nocturnal hemoglobinuria, N. Engl. J. Med. 355:1233-1243 (2006).
Hughes et al., Guillain-Barre syndrome, Lancet 366:1653-1666 (2005).
Jacobs et al., Detection and prevalence of alpha-latrotoxin-like effects of serum from patients with Guillain-Barre syndrome, Muscle Nerve 25:549-558 (2002).
Kaja et al., Severely impaired neuromuscular synaptic transmission causes muscle weakness in the Cacna1a-mutant mouse rolling Nagoya, Eur J. Neurosci 25:2009-2020 (2007).
Koski et al., Activation of terminal components of complement in patients with Guillain-Barre syndrome and other demyelinating neuropathies J. Clin. Invest 80:1492-1497 (1987).
Lange et al., Single-fiber electromyography shows terminal axon dysfunction in Miller Fisher syndrome: a case report, Muscle Nerve 34:232-234 (2006).
Ledeen, Gangliosides of the neuron, Trends in Neurosciences 8:169-174 (1985).
Lo, et al., Presynaptic neuromuscular transmission defect in the Miller Fisher syndrome, Neurology 66:148-149 (2006).
Morgan et al., The membrane attack pathway of complement drives pathology in passively induced experimental autoimmune myasthenia gravis in mice, Clin. Exp. Immunol. 146:294-302 (2006).
O'Hanlon et al., Anti-GQ1b ganglioside antibodies mediate complement-dependent destruction of the motor nerve terminal, Brain 124:893-906 (2001).
Plomp et al., Miller Fisher anti-GQ1b antibodies: alpha-latrotoxin-like effects on motor end plates, Ann. Neurol. 45:189-199 (1999).
Putzu et al., Immunohistochemical localization of cytokines, C5b-9 and ICAM-1 in peripheral nerve of Guillain-Barre syndrome, J. Neurol. Sci. 174:16-21 (2000).
Ramaglia et al., The membrane attack complex of the complement system is essential for rapid Wallerian degeneration, J. Neurosci. 27(29):7663-7672 (2007).
Rice, The interchangeability of the complement components of different animal species. I. literature survey, Can. J. Comp Med. 12:369-379 (1950).
Roberts et al., Serum factor in Miller-Fisher variant of Guillain-Barre syndrome and neurotransmitter release, Lancet 343:454-455 (1994).
Sanders et al., Activated terminal complement in cerebrospinal fluid in Guillain-Barre syndrome and multiple sclerosis, J. Immunol. 136:4456-4459 (1986).
Sartucci, et al., Electrophysiological evidence by single fibre electromyography of neuromuscular transmission impairment in a case of Miller Fisher syndrome, Neurol. Sci. 26:125-128 (2005).
Schwarz et al., The localization of gangliosides in neurons of the central nervous system: The use of anti-ganglioside antibodies, Biochimica et Biophysica Acta—Reviews on Biomembranes 1286:247-267 (1996).
Susuki et al., Anti-GM1 antibodies cause complement-mediated disruption of sodium channel clusters in peripheral motor nerve fibers, J. Neurosci. 27(15):3956-3967 (2007).
Thomas et al., Inhibition of complement activity by humanized anti-C5 antibody and single-chain Fv, Mol. Immunol. 33(17/18):1389-1401 (1996).
Uncini et al., Fisher syndrome with tetraparesis and antibody to GQ1b: evidence for motor nerve terminal block, Muscle Nerve 22:640-644 (1999).
Van Koningsveld et al., A clinical prognostic scoring system for Guillain-Barre syndrome, Lancet Neurol. 6:589-594 (2007).
Willison et al., The immunopathogenesis of Miller Fisher syndrome, J. Neuroimmunol. 100:3-12 (1999).
Willison et al., Peripheral neuropathies and anti-glycolipid antibodies, Brain 125:2591-2625 (2002).
Wirguin et al., Presynaptic neuromuscular transmission block in Guillain-Barre syndrome associated with anti-GQ1$_b$ antibodies, Neuromuscul. Disord. 12:292-293 (2002).
Wurzner et al., Inhibition of terminal complement complex formation and cell lysis by monoclonal antibodies, Complement Inflamm. 8:328-340 (1991).
Yuki, Infectious origins of, and molecular mimicry in, Guillain-Barre and Fisher syndromes, Lancet Infect. Dis. 1:29-37 (2001).

\* cited by examiner

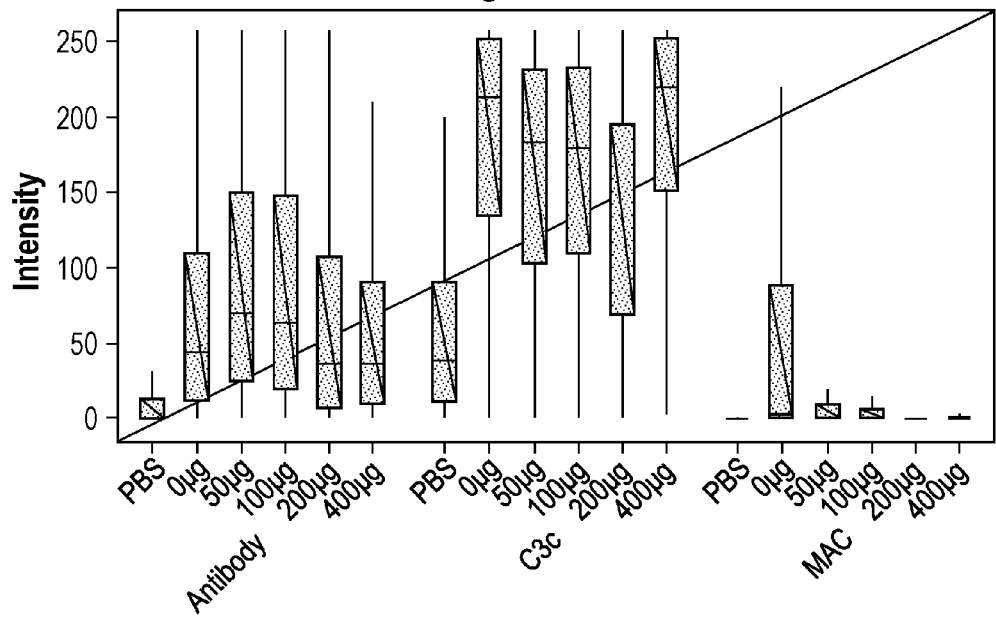
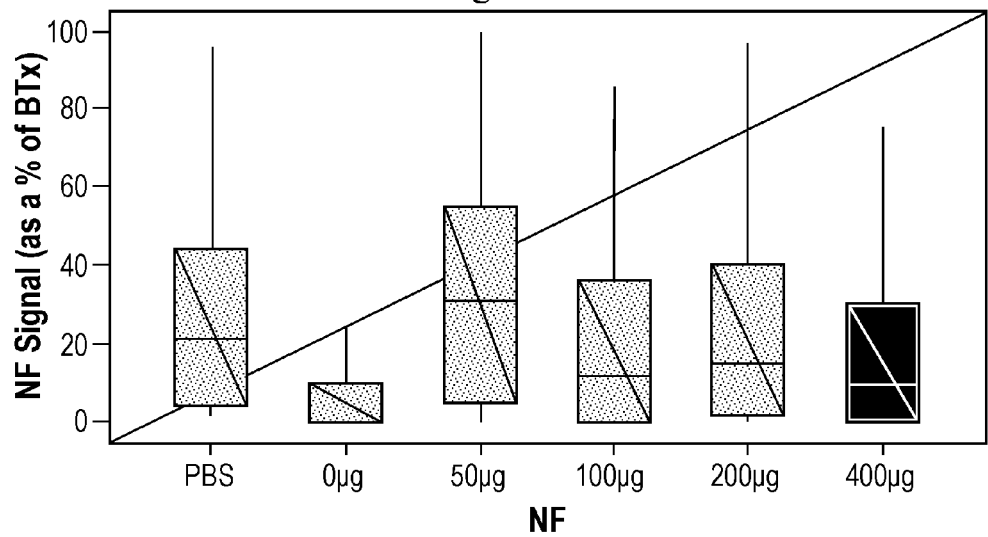

METHODS AND COMPOSITIONS FOR THE TREATMENT OF ANTIBODY MEDIATED NEUROPATHIES

CROSS-REFERENCE TO RELATED APPLICATIONS

This application is a national stage filing under 35 U.S.C. 371 of International Application PCT/US2007/019416, filed Sep. 5, 2007, which claims the benefit of U.S. Application No. 60/842,296 filed Sep. 5, 2006, the specifications of which are incorporated by reference herein. International Application PCT/US2007/019416 was published under PCT Article 21(2) in English.

FIELD OF THE INVENTION

This application provides methods and compositions for the treatment of antibody mediated neuropathies that activate complement to induce nerve injury. In specific embodiments, the application relates to the use of complement cascade inhibitors as therapeutic agents to treat antibody mediated neuropathies.

BACKGROUND OF THE INVENTION

Neuropathy is a generic term used to describe diseases of the peripheral nervous system. There are about 200 known different causes of peripheral neuropathies. Although most neuropathies affect all three major classes of nerve fibers to varying degrees, some diseases involve only one or two, and are thus said to be purely or predominantly motor, sensory, or autonomic neuropathies.

Guillain-Barré syndrome (GBS) is an acute illness involving the peripheral nervous system that usually occurs two to three weeks after a flu-like disease or other infection, including *Campylobacter enteritis*. It is mostly a motor neuropathy, meaning that its symptoms are largely related to the involvement of the motor nerves. Despite the primarily motor nature of the disease, the earliest symptoms may be numbness and tingling felt in the lower extremities followed shortly by weakness of the distal muscles of the lower extremities. The danger occurs when the weakness involves the muscles of respiration. GBS is associated in a proportion of cases with antiganglioside autoantibodies (AGAs) to a wide range of specific glycolipid structures, and also with antibodies to other nerve components including myelin proteins and glycosaminoglycans in some cases, and in other GBS cases, antibodies are presumed to be present but have yet to be formally identified.

Miller Fisher syndrome (MFS) is a variant of Guillain-Barré syndrome, accounting for 5-10% of cases. In one survey, the annual incidence has been estimated at 0.09 per 100,000 population. MFS is characterized by the acute onset of opthalmoplegia, ataxia and areflexia. Anti-GQ1b ganglioside antibodies are the serological hallmark of MFS. The antibodies may arise in some cases through molecular mimicry with *Campylobacter* lipopolysaccharides. It is now widely accepted that well over 90% of patients with MFS have anti-GQ1b IgG antibodies during the acute phase of the illness. Equally significant is the complete absence of anti-GQ1b IgG antibodies from normal and other disease control groups, indicative of a high level of specificity for this disease association. The antibody titers peak at clinical presentation, decaying rapidly with the course of clinical recovery. Anti-GQ1b IgG antibody titers are also elevated in the acute phase sera of some patients with Guillain-Barré syndrome with opthalmoplegia. The anti-GQ1b IgG antibody marker also identifies a cluster of closely related syndromes, often considered formes frustes of MFS, that have in common the presence of external opthalmoplegia or cerebellar-like ataxia.

The current treatment for GBS, including AGA-mediated cases is intravenous immunoglobulin (IVIg), plasma exchange, or a combination of both. Although some neuropathies like GBS are usually self-limiting illnesses, intensive therapeutic intervention is often needed. Some individuals are left with residual deficits. Other neuropathies are chronic and only symptoms such as pain are treated. There is a great need for additional treatments to improve symptoms and decrease recovery time of antibody mediated neuropathies.

SUMMARY OF THE INVENTION

Methods and compositions for treating patients suffering from antibody-mediated neuropathies are presented. In certain embodiments, a method of treating an antibody mediated neuropathy in a mammal comprises administering to the mammal a therapeutically effective amount of a complement cascade inhibitor.

In a number of neuropathies antibodies to specific components of nerves have been identified. Some of these diseases are mediated by anti-ganglioside and anti-glycolipid autoantibodies such as the Miller Fisher variant of Guillain-Barré syndrome. Antibodies to a wide range of glycolipids including GM1, GM1(NeuGc), GM1b, GalNAc-GM1b, GD1a, GalNAc-GD1a, GD1b, 9-O-acetyl GD1b, GD3, GT1a, GT1b, GQ1b, GQ1ba, LM1, galactocerebroside and SGPG have been reported in papers on inflammatory neuropathies, as case reports and in larger series. In an exemplary embodiment, a method of treating an AGA mediated neuropathy in a mammal comprises administering to the mammal a therapeutically effective amount of a complement cascade inhibitor such as an anti-C5 antibody.

Antibodies to other nerve components including proteins and glycoproteins have also been reported to be causative in neuropathies. For example, monoclonal IgM against myelin-associated glycoprotein causes anti-MAG IgM paraproteinemic neuropathy (Willison and Yuki, Brain, 2002, 125, 2591-2625). In a proportion of neuropathy cases, antibodies are presumed to be present owing to similar pathological patterns and treatment responses as seen in antibody-associated cases, but the specificity of the presumed antibody has yet to be formally identified. In certain embodiments, the antibody mediated neuropathy may be one or more of the following: acute motor axonal neuropathy, acute inflammatory demyelinating polyneuropathy, Bickerstaff's brainstem encephalitis, acute opthalmoparesis, ataxic Guillain-Barré syndrome, pharyngeal-cervical-brachial weakness, chronic neuropathy syndromes with anti-glycolipid antibodies, anti-MAG IgM paraproteinemic neuropathy, chronic sensory ataxic neuropathy with anti-disialosyl antibodies, IgM, IgG and IgA paraproteinemic neuropathy, motor neuropathy with anti-GM1 and anti-GM2 antibodies, chronic inflammatory demyelinating neuropathy (CIDP), multifocal motor neuropathy (MMN), and multifocal acquired demyelinating sensory and motor neuropathy (MADSAM).

In some neuropathies the activation of complement may be antibody-independent, for example, in hereditary amyloid neuropathy. In this disease, early classical pathway activation markers, C1q and C4, have been detected in amyloid deposits in the absence of detectable antibody (Hafer-Macko et al., J Peripher Nery Syst. 2000 September; 5(3):131-9; incorporated herein by reference). This suggests that antibody-independent activation of the classical pathway can occur and that complement cascade inhibitors may be effective in treating antibody-independent, complement mediated neuropathies. In an exemplary embodiment, a method of treating an antibody-independent, complement mediated neuropathy in a mammal comprises administering to the mammal a therapeutically effective amount of a complement cascade inhibitor. In certain embodiments, an antibody of the application inhibits activation of the classical pathway, the alternative pathway or the lectin complement pathway. In certain embodiments, said antibody is an antibody against any member of the group comprising the complement components C5, C5b, C6, C7, C8, and C9. In certain embodiments, said antibody is an antibody against C5. In certain embodiments, said antibody is an inhibitor of C5 cleavage.

In certain embodiments, a complement cascade inhibitor of the application is selected from: a polypeptide, a polypeptide analog, a peptidomimetic, an antibody, a nucleic acid, an RNAi construct, a nucleic acid analog, and a small molecule.

In certain embodiments, an antibody of the application is a whole antibody or an antibody fragment. In certain embodiments, said whole antibody or antibody fragment is selected from the group consisting of: a polyclonal antibody, a monoclonal antibody or antibody fragment, a diabody, a chimerized or chimeric antibody or antibody fragment, a humanized antibody or antibody fragment, a deimmunized human antibody or antibody fragment, a fully human antibody or antibody fragment, a single chain antibody, an Fv, an Fab, an Fab', or an F(ab')$_2$.

In certain embodiments, an antibody of the application inhibits activation of the classical pathway, the alternative pathway or the lectin complement pathway. In certain embodiments, said antibody is an antibody against any member of the group comprising the complement components C5, C5b, C6, C7, C8, and C9. In certain embodiments, said antibody is an antibody against C5. In certain embodiments, said antibody is an inhibitor of C5 cleavage.

In certain embodiments, an antibody of the application is eculizumab. In certain embodiments, said antibody is pexelizumab. In certain embodiments, said treatment with eculizumab is chronic. In certain embodiments, said treatment with pexelizumab comprises treating an acute episode.

In certain embodiments, a mammal of the application is treated by administering said antibody intravenously. In certain embodiments, said antibody is administered systemically to said mammal. In certain embodiments, said agent is administered locally to said mammal.

In certain embodiments, treatments of the application result in decreased neural injury in a mammal of the application.

In certain embodiments, a mammal of the application is treated to inhibit or decrease the amount and/or extent of an undesirable physiological condition resulting from excess nerve injury due to antibody dependent neuropathy. In certain embodiments, said undesirable physiological condition is selected from the group consisting of opthalmoplegia, ataxia, areflexia, abnormal muscle coordination, paralysis of the eye muscles, aching pain in the muscles, absence of the tendon reflexes, numbness and tingling felt in the lower extremities, weakness of the distal muscles of the lower extremities, a footdrop, weakness involving the entire lower extremities, weakness involving the upper extremities, weakness in the muscles of respiration, and death.

In certain embodiments, methods of the application result in decreased membrane attack complex (MAC) formation at presynaptic motor axons.

In certain embodiments, methods of the application result in restoration of a normal frequency of miniature endplate potentials.

In certain embodiments, methods of the application result in restoration of synaptic transmission at the neuromuscular junctions.

In certain embodiments, methods of the application result in decreased loss of terminal integrity at the neuromuscular junctions.

In another embodiment, a method of treating Guillain-Barré syndrome in a mammal comprises administering to the mammal a therapeutically effective amount of a complement cascade inhibitor such as an anti-05 antibody. In another embodiment, a method of treating the Miller Fisher variant of Guillain-Barré syndrome in a mammal comprises administering to the mammal a therapeutically effective amount of a complement cascade inhibitor such as an anti-05 antibody.

BRIEF DESCRIPTION OF THE DRAWINGS

FIG. 1A shows tissues treated with NHS/eculizumab showed intense C3c staining at neuromuscular junctions (NMJs), similar to that of NHS/control mAb-treated tissues (p=0.12). FIG. 1B shows that membrane attack complex (MAC) staining was not observed in the presence of eculizumab (intensity comparable to baseline, p=0.92), indicating complete inhibition of terminal complement. FIG. 1C shows that axonal integrity was preserved in the presence of eculizumab, as assessed by the presence of neurofilament (NF) signal, comparable to baseline in untreated controls (p=0.80). FIGS. 4D, 4E and 4F are illustrative immunofluorescent images of NMJs in whole-mount muscle demonstrating the protective effect of eculizumab against MAC deposition (FIG. 4D), perisynaptic Schwann cell (pSC) damage (FIG. 4E) and terminal motor axonal damage (FIG. 4F), as compared to NHS/control mAb treatment. Postsynaptic nicotinic acetylcholine receptor (nAChR; purple) staining was used to delineate the NMJ. Intermediate complement protein C3c (FIG. 4D) remains abundantly deposited at NMJs. *p<0.01, different from untreated; #p<0.01, different from control mAb-treated; scale bar=20 μm.

FIG. 2A shows spontaneous uniquantal acetylcholine release, measured as MEPP frequency, at the NMJ. Eculizumab prevented the induction of a high MEPP frequency (p<0.001, n=5 muscles). FIG. 2B shows representative 1 s duration traces obtained during incubation with NHS, either with added eculizumab (upper trace) or control mAb (lower trace). FIG. 2C shows asynchronous twitching of muscle fibers induced by NHS was largely prevented by eculizumab (p<0.01, n=5 muscles). FIG. 2D shows that eculizumab completely prevented the occurrence of 'silent'

NMJs (i.e. without detectable synaptic electrophysiological signals). For FIGS. 2E, 2F and 2G hemi-diaphragm muscle-nerve preparations were pre-incubated with 200 μg/ml CGM3 and the protective effect of several concentrations of eculizumab (0-100 μg/ml, n=2-5 muscles per concentration) added to the NHS was observed in muscle contraction force recording experiments. FIG. 2E shows examples of the contraction profiles observed at 0, 30, 60 and 90 min after the start of the NHS incubation with either no eculizumab added or 6 or 100 μg/ml eculizumab added. Each contraction was elicited by supramaximal electric stimulation of the phrenic nerve for 3 s at 40 Hz. FIG. 2F shows development of the contraction loss during NHS incubation with the various concentrations of eculizumab added. FIG. 2G shows the concentration-effect relationship of eculizumab and the protection against loss of contraction after 90 min after the start of the NHS incubation. A Boltzmann sigmoidal curve is fitted through the data points, yielding an $EC_{50}$ of 7.1 μg/ml. Error bars in FIGS. 2A, 2D, 2F and 2G represent S.E.M.

FIGS. 3A-3B show eculizumab dose response curve in vivo. FIG. 3A shows that an increasing dose of eculizumab results in a dose-dependent reduction in MAC deposition at the NMJ. FIG. 3B shows the neurofilament signal and demonstrates preservation of axonal integrity at all doses of eculizumab investigated when compared to PBS treated baseline control.

FIGS. 4A-4H show that respiratory paralysis in the in vivo MFS model is prevented by eculizumab due to inhibition of presynaptic block of neuromuscular transmission in the diaphragm. Mice (n=6) were intraperitoneally injected with 1.5 mg anti-GQ1b ganglioside mAb CGM3 and, 16 h later, with 0.5 ml 100% normal human serum (NHS) as complement source. A dose of 200 μg eculizumab or control mAb was injected in the tail vein shortly before the NHS injection. FIG. 4A shows grip-strength analysis at 2 h post-NHS injection. Eculizumab prevented the loss of pulling force observed in the control mAb group (p<0.01). FIG. 4B shows average tidal volume and FIG. 4C shows breathing rate measured with whole-body plethysmography before NHS injection and during the $2^{nd}$, $4^{th}$ and $6^{th}$ hour post-NHS injection. The development of breathing difficulty was prevented by eculizumab. FIG. 4D shows examples of 1 s traces of plethysmography signals obtained in eculizumab- and control mAb-treated mice. FIG. 4E shows twitch force and FIG. 4F shows tetanic force elicited in the dissected diaphragm muscle by single and 40 Hz electrical nerve stimulation, respectively. Eculizumab completely prevented the severe paralysis observed in muscles from control mAb-treated mice (p<0.01). FIG. 4G shows that eculizumab almost completely prevented the occurrence of 'silent' NMJs (i.e. without detectable synaptic electrophysiological signals) in these mice (p<0.001). FIG. 4H shows thirty superimposed representative traces of 1 s duration obtained in NMJs of muscle from eculizumab-treated (upper traces) or control mAb-treated (lower traces) mice. Error bars in the bar graphs of these figures represent S.E.M.

FIGS. 5A and 5B show that C3c and membrane attack complex (MAC) deposition is reduced at neuromuscular junctions (NMJs) of both eculizumab- and control mAb-treated mice (p<0.01). FIG. 5C shows that neurofilament (NF) signal was significantly greater at NMJs of muscles from eculizumab-treated mice, compared with control (p<0.01). FIGS. 5D and 5E show illustrative immunofluorescent images of NMJs in whole mount muscle. Postsynaptic nicotinic acetylcholine receptors (nAChR; purple) staining was used to delineate NMJs. FIG. 5D further shows C3c and MAC deposition. FIG. 5E further shows NF integrity and MAC deposition. FIG. 5F is an electron micrograph of eculizumab-protected nerve terminals with tightly packed synaptic vesicle and electron dense mitochondria with parallel cristae. At NMJs from control mAb-treated mice, nerve terminals are electron lucent with sparse synaptic vesicles and swollen mitochondria. #p<0.01, different from control mAb-treated. Scale bars in FIGS. 5D and 5E=20 μm; and in FIG. 5F=1 μm.

DETAILED DESCRIPTION OF THE INVENTION

Overview

Figure 1:
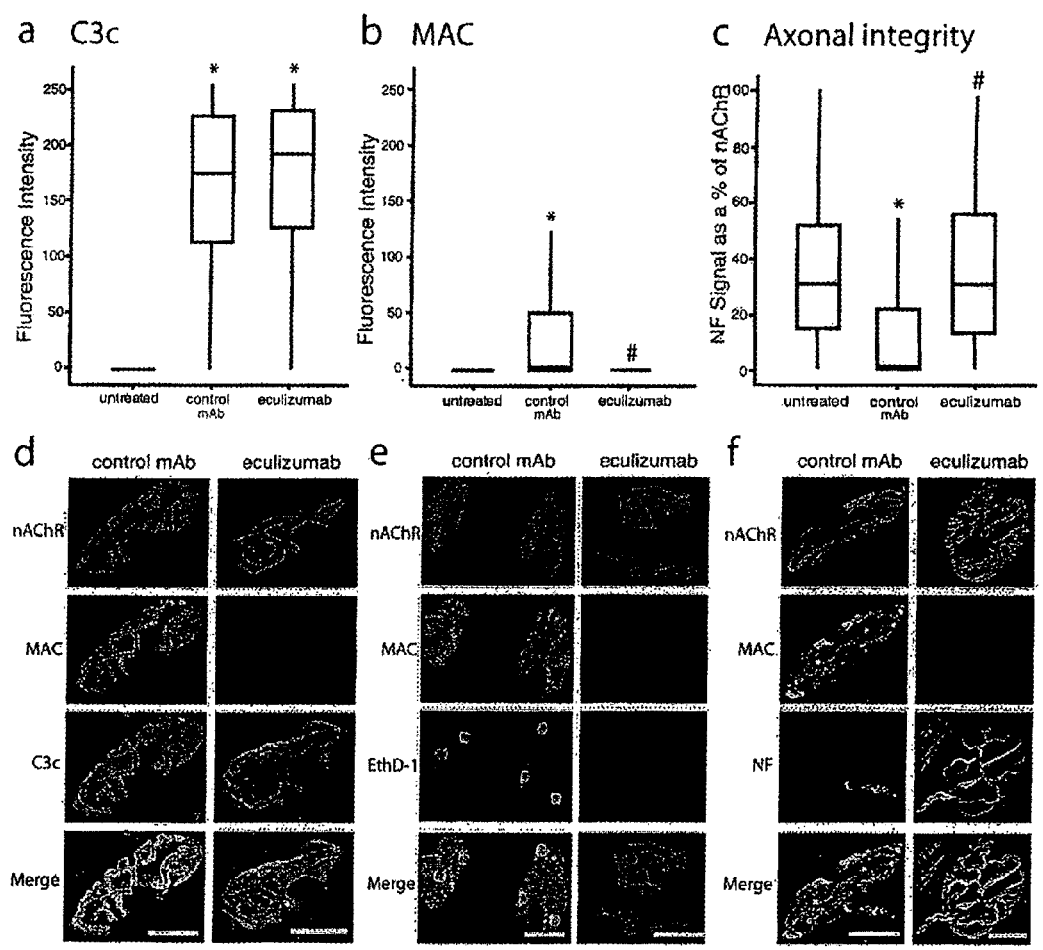
FIGS. 1A-1F show an immunohistological demonstration of the protective effect of eculizumab against MAC deposition and terminal motor axonopathy at NMJs in the in vitro MFS model. Mouse hemi-diaphragm preparations were pre-incubated with anti-GQ1b ganglioside mAb CGM3 (50 μg/ml) and subsequently treated with 40% normal human serum (NHS) with either added eculizumab (anti-human C5 neutralizing mAb; 100 μg/ml) or non-specific isotype-matched control mAb (100 μg/ml), and compared with untreated tissue.

It is here proposed that treatment of an antibody mediated neuropathy patient with a complement inhibitor will attenuate neural injury. For example, the antibody mediated neuropathy may be an AGA mediated neuropathy. Inhibitors of members of the complement cascade include, for example, antibodies to components such as C5, C5b, C6, C7, C8, and C9. In particular embodiments, this application contemplates the use of the anti-C5 antibody eculizumab (a whole antibody) which is known to inhibit cleavage of C5 into C5a and C5b. Treatment of patients with such inhibitors thereby decreases complement mediated neural injury. Eculizumab has been used in clinical studies and found to be well tolerated with minimal side effects. See U.S. Pat. No. 6,355,245 and Hillmen et al., New Engl. J. Med. 350:552-559 (2004), the contents of which are specifically incorporated herein by reference.

The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins (which are also found in most other body fluids, such as lymph, bone marrow, synovial fluid, and cerebrospinal fluid) make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components and, while they differ in their early steps, both converge and share the same terminal complement components responsible for the destruction of target cells and viruses.

The classical complement pathway is typically initiated by antibody recognition of and binding to an antigenic site on a target cell. This surface bound antibody subsequently reacts with the first component of complement, C1. The C1 thus bound undergoes a set of autocatalytic reactions that result in, inter alia, the induction of C1 proteolytic activity acting on complement components C2 and C4.

This activated C1 cleaves C2 and C4 into C2a, C2b, C4a, and C4b. The function of C2b is poorly understood. C2a and C4b combine to form the C4b,2a complex, which is an active protease known as classical C3 convertase. C4b,2a acts to cleave C3 into C3a and C3b. C3a and C4a are both relatively weak anaphylatoxins that may induce degranulation of mast cells, resulting in the release of histamine and other mediators of inflammation.

C3b has multiple functions. As opsonin, it binds to bacteria, viruses and other cells and particles and tags them for removal from the circulation. C3b can also form a complex with C4b, C2a to produce C4b,2a,3b, or classical C5 convertase, which cleaves C5 into C5a (another anaphylatoxin) and C5b. Alternative C5 convertase is C3b,Bb,C3b and performs the same function. C5b combines with C6 yielding C5b,6, and this complex combines with C7 to form the ternary complex C5b,6,7. The C5b,6,7 complex binds C8 at the surface of a cell membrane. Upon binding of C9, the complete membrane attack complex (MAC) is formed (C5b-9) which mediates the lysis of foreign cells, microorganisms, and viruses.

Further discussions of the classical complement pathway, as well as a detailed description of the alternative pathway of complement activation, can be found in numerous publications including, for example, Muller-Eberhard, Annu Rev Biochem. 1988; 57:321-47.

Inhibitors of the Complement Cascade

In certain embodiments, a complement inhibitor may be a small molecule (up to 6,000 Da in molecular weight), a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors.

In certain embodiments, a complement inhibitor may be a protein or protein fragment. Proteins are known which inhibit the complement cascade, including CD59, CD55, CD46 and other inhibitors of C8 and C9 (see, e.g., U.S. Pat. No. 6,100,443). Proteins known as complement receptors and which bind complement are also known (see, Published PCT Patent Application WO 92/10205 and U.S. Pat. No. 6,057,131). Use of soluble forms of complement receptors, e.g., soluble CR1, can inhibit the consequences of complement activation such as neutrophil oxidative burst, complement mediated neural injury, and C3a and C5a production. Those of skill in the art recognize the above as some, but not all, of the known methods of inhibiting complement and its activation.

In certain embodiments, a complement inhibitor may be an antibody capable of inhibiting complement, such as an antibody that can block the formation of MAC. For example, an antibody complement inhibitor may include an anti-C5 antibody. Such anti-C5 antibodies may directly interact with C5 and/or C5b, so as to inhibit the formation of and/or physiologic function of C5b.

Suitable anti-C5 antibodies are known to those of skill in the art. Antibodies can be made to individual components of activated complement, e.g., antibodies to C7, C9, etc. (see, e.g., U.S. Pat. No. 6,534,058; published U.S. patent application US 2003/0129187; and U.S. Pat. No. 5,660,825). U.S. Pat. No. 6,355,245 teaches an antibody which binds to C5 and inhibits cleavage into C5a and C5b thereby decreasing the formation not only of C5a but also the downstream complement components.

The concentration and/or physiologic activity of C5a and C5b in a body fluid can be measured by methods well known in the art. For C5a such methods include chemotaxis assays, RIAs, or ELISAs (see, for example, Ward and Zvaifler, J Clin Invest. 1971 March; 50(3):606-16; Wurzner, et al., Complement Inflamm. 8:328-340, 1991). For C5b, hemolytic assays or assays for soluble C5b-9 as discussed herein can be used. Other assays known in the art can also be used. Using assays of these or other suitable types, candidate antibodies capable of inhibiting complement such as anti-05 antibodies, now known or subsequently identified, can be screened in order to 1) identify compounds that are useful in the practice of the application and 2) determine the appropriate dosage levels of such compounds.

An antibody capable of inhibiting complement such as an anti-C5 antibody affecting C5b is preferably used at concentrations providing substantial reduction (i.e., reduction by at least about 25% as compared to that in the absence of the anti-05 antibody) in the C5b levels present in at least one blood-derived fluid of the patient following activation of complement within the fluid. Such concentrations can be conveniently determined by measuring the cell-lysing ability (e.g., hemolytic activity) of complement present in the fluid or the levels of soluble C5b-9 present in the fluid. Accordingly, a specific concentration for an antibody that affects C5b is one that results in a substantial reduction (i.e., a reduction by at least about 25%) in the cell-lysing ability of the complement present in at least one of the patient's blood-derived fluids. Reductions of the cell-lysing ability of complement present in the patient's body fluids can be measured by methods well known in the art such as, for example, by a conventional hemolytic assay such as the hemolysis assay described by Kabat and Mayer (eds.), "Experimental Immunochemistry, 2d Edition", 135-240, Springfield, Ill., C C Thomas (1961), pages 135-139, or a conventional variation of that assay such as the chicken erythrocyte hemolysis method described below.

Specific antibodies capable of inhibiting complement, such as an anti-05 antibody, are relatively specific and do not block the functions of early complement components. In particular, such specific agents will not substantially impair the opsonization functions associated with complement component C3b, which functions provide a means for clearance of foreign particles and substances from the body.

C3b is generated by the cleavage of C3, which is carried out by classical and/or alternative C3 convertases and results in the generation of both C3a and C3b. Therefore, in order not to impair the opsonization functions associated with C3b, specific antibodies capable of inhibiting complement downstream of C3, such as an anti-C5 antibody, do not substantially interfere with the cleavage of complement component C3 in a body fluid of the patient (e.g., serum) into C3a and C3b. Such interference with the cleavage of C3 can be detected by measuring body fluid levels of C3a and/or C3b, which are produced in equimolar ratios by the actions of the C3 convertases. Such measurements are informative because C3a and C3b levels will be reduced (compared to a matched sample without the antibody capable of inhibiting complement such as an anti-05 antibody) if cleavage is interfered with by an antibody capable of inhibiting complement.

In practice, the quantitative measurement of such cleavage is generally more accurate when carried out by the measurement of body fluid C3a levels rather than of body fluid C3b levels, since C3a remains in the fluid phase whereas C3b is rapidly cleared. C3a levels in a body fluid can be measured by methods well known in the art such as, for example, by using a commercially available C3a EIA kit, e.g., that sold by Quidel Corporation, San Diego, Calif., according to the manufacturer's specifications. Particularly specific antibodies capable of inhibiting complement such as an anti-05 antibody produce essentially no reduction in body fluid C3a levels following complement activation when tested in such assays.

Certain antibodies of the disclosure will prevent the cleavage of C5 to form C5a and C5b, thus preventing the generation of the anaphylatoxic activity associated with C5a and preventing the assembly of the membrane attack complex associated with C5b. As discussed above, in a particular embodiment, these anti-05 antibodies will not impair the opsonization function associated with the action of C3b.

A preferred method of inhibiting complement activity is to use a monoclonal antibody which binds to complement C5 and inhibits cleavage. This decreases the formation of both C5a and C5b while at the same time allowing the formation of C3a and C3b which are beneficial to the recipient. Such antibodies which are specific to human complement are known (U.S. Pat. No. 6,355,245). These antibodies disclosed in U.S. Pat. No. 6,355,245 include a preferred whole antibody (now named eculizumab). A similar antibody against mouse C5 is called BB5.1 (Frei et al., Mol. Cell. Probes. 1:141-149 (1987)). Antibodies to inhibit complement activity need not be monoclonal antibodies. They can be, e.g., polyclonal antibodies. They may additionally be antibody fragments. An antibody fragment includes, but is not limited to, an Fab, F(ab'), F(ab')$_2$, single-chain antibody, and Fv. Furthermore, it is well known by those of skill in the art that antibodies can be humanized (Jones et al., Nature 321:522-5 (1986)), chimerized, or deimmunized. The antibodies to be used in the present disclosure may be any of these. It is preferable to use humanized antibodies.

In specific embodiments, a therapeutic agent of the disclosure comprises an antibody or antibody fragment. Antibodies and fragments thereof may be made by any conventional method, such as those methods described herein. Antibodies are found in multiple forms, e.g., IgA, IgG, IgM, etc. Additionally, antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

This invention provides fragments of anti-C5 antibodies, which may comprise a portion of an intact antibody, preferably the antigen-binding or variable region of the intact antibody. Examples of antibody fragments include Fab, Fab', F(ab')$_2$, and Fv fragments; diabodies; linear antibodies (Zapata et al., Protein Eng. 8:1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although likely at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv see Pluckthun in *The Pharmacology of Monoclonal Antibodies*, vol. 113, Rosenburg and Moore, eds. (Springer-Verlag: New York, 1994), pp. 269-315.

SMIPs are a class of single-chain peptide engineered to include a target binding region, effector domain (CH2 and CH3 domains). See, e.g., U.S. Patent Application Publication No. 20050238646. The target binding region may be derived from the variable region or CDRs of an antibody, e.g., an anti-C5 antibody of the application. Alternatively, the target binding region is derived from a protein that binds C5.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (C. A. Janeway et al., *Immunobiology* 5th edition, page 147, Garland Publishing (New York, 2001)).

This disclosure also provides monoclonal anti-C5 antibodies. A monoclonal antibody can be obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are often synthesized by the hybridoma culture, uncontaminated by other immunoglobulins. Monoclonal antibodies may also be produced in transfected cells, such as CHO cells and NS0 cells. The modifier "monoclonal" indicates the character of the antibody as being obtained from a substantially homogeneous population of antibodies and does not require production of the antibody by any particular method. For example, the monoclonal antibodies to be used in accordance with the present disclosure may be made by the hybridoma method first described by Kohler et al., Nature 256:495-497 (1975), or may be made by recombinant DNA methods (see, e.g., U.S. Pat. Nos. 4,816,567 and 6,331,415). The "monoclonal antibodies" may also be isolated from phage antibody libraries using the techniques described in Clackson et al., Nature 352:624-628 (1991) and Marks et al., J. Mol. Biol. 222:581-597 (1991), for example.

A description of the preparation of a mouse anti-human-05 monoclonal antibody with specific binding characteristics is presented in U.S. Patent Application Publication No. 20050226870. Wurzner et al., Complement Inflamm. 8:328-340 (1991), describe the preparation of other mouse anti-human-05 monoclonal antibodies referred to as N19-8 and N20-9.

Other antibodies specifically contemplated are "oligoclonal" antibodies. As used herein, the term "oligoclonal" antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule (e.g., C5). In view of the assays and epitopes disclosed herein, those skilled in the art can generate or select antibodies or mixtures of antibodies that are applicable for an intended purpose and desired need.

In certain embodiments that include a humanized and/or chimeric antibody, one or more of the CDRs are derived from an anti-human C5 antibody. In a specific embodiment, all of the CDRs are derived from an anti-human C5 antibody. In another specific embodiment, the CDRs from more than one anti-human C5 antibody are mixed and matched in a chimeric antibody. For instance, a chimeric antibody may comprise a CDR1 from the light chain of a first anti-human C5 antibody combined with CDR2 and CDR3 from the light chain of a second anti-human C5 antibody, and the CDRs from the heavy chain may be derived from a third anti-human C5 antibody. Further, the framework regions may be derived from one of the same anti-human C5 antibodies, from one or more different antibodies, such as a human antibody, or from a humanized antibody. Human or humanized antibodies are specific for administration to human patients.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology 10:1455-1460 (1992), regarding primatized antibody. See, e.g., Ladner et al., U.S. Pat. No. 4,946,778; and Bird et al., Science 242:423-426 (1988), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Preferred functional fragments retain an antigen-binding function of a corresponding full-length antibody (such as for example, ability of anti-C5 antibody to bind C5).

General methods for the immunization of animals (in this case with C5 and/or C5b, etc.), isolation of antibody producing cells, fusion of such cells with immortal cells (e.g., myeloma cells) to generate hybridomas secreting monoclonal antibodies, screening of hybridoma supernatants for reactivity of secreted monoclonal antibodies with a desired antigen (in this case the immunogen or a molecule containing the immunogen), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz et al., Cellular Immunol. 127:337-351 (1990); Wurzner et al., Complement Inflamm. 8:328-340 (1991); and Mollnes et al., Scand. J. Immunol. 28:307-312 (1988).

Pharmaceutical Formulations and Uses

Methods of administration of small molecules, proteins, and nucleic acids are well-known to those of skill in the art. Methods of administration of antibodies are well-known to those of skill in the art. To achieve the desired inhibition, the antibodies can be administered in a variety of unit dosage forms. The dose will vary according to the particular antibody. For example, different antibodies may have different masses and/or affinities, and thus require different dosage levels. Antibodies prepared as Fab fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, and preferably between about 5 mg per kg and about 50 mg per kg per patient per treatment. In terms of plasma concentrations, the antibody concentrations are preferably in the range from about 25 µg/mL to about 500 µg/mL. However, greater amounts may be required for extreme cases and smaller amounts may be sufficient for milder cases.

Administration of the anti-C5 antibodies will generally be performed by an intravascular route, e.g., via intravenous infusion by injection. Other routes of administration may be used if desired but an intravenous route will be the most preferable. Formulations suitable for injection are found in Remington's Pharmaceutical Sciences, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

Administration of the antibodies capable of inhibiting complement such as an anti-05 antibody will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody capable of inhibiting complement to be administered. Antibodies capable of inhibiting complement such as an anti-05 antibody can also be administered in a variety of unit dosage forms and their dosages will also vary with the size, potency, and in vivo half-life of the particular antibody capable of inhibiting complement being administered. Doses of antibodies capable of inhibiting complement such as an anti-05 antibody will also vary depending on the manner of administration, the particular symptoms of the patient being treated, the overall health, condition, size, and age of the patient, and the judgment of the prescribing physician.

In certain embodiments, a typical therapeutic treatment includes a series of doses, which will usually be administered concurrently with the monitoring of clinical endpoints with the dosage levels adjusted as needed to achieve the desired clinical outcome. In certain embodiments, treatment is administered in multiple dosages over at least a week. In certain embodiments, treatment is administered in multiple dosages over at least a month. In certain embodiments, treatment is administered in multiple dosages over at least a year. In certain embodiments, treatment is administered in multiple dosages over the remainder of the patient's life.

The frequency of administration may also be adjusted according to various parameters. These include the clinical response, the plasma half-life of the therapeutic of the disclosure, and the levels of the antibody in a body fluid, such as, blood, plasma, serum, or synovial fluid. To guide adjustment of the frequency of administration, levels of the therapeutic of the disclosure in the body fluid may be monitored during the course of treatment.

In certain embodiments, the frequency of administration may be adjusted according to an assay measuring cell-lysing ability of complement present in one or more of the patient's body fluids. The cell-lysing ability can be measured as percent hemolysis in hemolytic assays of the types described herein. A 10% or 25% or 50% reduction in the cell-lysing ability of complement present in a body fluid after treatment with the antibody capable of inhibiting complement used in the practice of the application means that the percent hemolysis after treatment is 90, 75, or 50 percent, respectively, of the percent hemolysis before treatment.

For the treatment of antibody mediated neuropathies by systemic administration of an antibody capable of inhibiting complement such as an anti-05 antibody (as opposed to local administration), administration of a large initial dose is specific, i.e., a single initial dose sufficient to yield a substantial reduction, and more preferably an at least about 50% reduction, in the hemolytic activity of the patient's serum. Such a large initial dose is preferably followed by regularly repeated administration of tapered doses as needed to maintain substantial reductions of serum hemolytic titer. In another embodiment, the initial dose is given by both local and systemic routes, followed by repeated systemic administration of tapered doses as described above. For administration of an anti-C5 antibody to humans, see, e.g., Hillmen et al., N. Engl. J. Med. 350:552-559 (2004). The levels of antibody administered in Hillmen et al. are based on half-life of the antibody and are relevant to administration of an anti-C5 antibody for other indications such as for treating neuropathies.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin.

Formulations of the subject antibodies include those suitable for oral, dietary, topical, parenteral (e.g., intravenous, intraarterial, intramuscular, subcutaneous injection), opthalmologic (e.g., topical or intraocular), inhalation (e.g., intrabronchial, intranasal or oral inhalation, intranasal drops), rectal, and/or intravaginal administration. Other suitable methods of administration can also include rechargeable or biodegradable devices and controlled release polymeric devices. Stents, in particular, may be coated with a controlled release polymer mixed with an agent of the application. The pharmaceutical compositions of this disclosure can also be administered as part of a combinatorial therapy with other agents (either in the same formulation or in a separate formulation).

The amount of the formulation which will be therapeutically effective can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no no downward adjustment to "ideal" weight. In such a situation, an appropriate dose may be calculated by the following formula: Dose (mL)=[patient weight (kg)×dose level (mg/kg)/drug concentration (mg/mL)]

To achieve the desired treatment results, anti-C5 antibodies can be administered in a variety of unit dosage forms. The dose will vary according to the particular antibody. For example, different antibodies may have different masses and/or affinities, and thus require different dosage levels. Antibodies prepared as Fab' fragments or single chain antibodies will also require differing dosages than the equivalent native immunoglobulins, as they are of considerably smaller mass than native immunoglobulins, and thus require lower dosages to reach the same molar levels in the patient's blood.

Other therapeutics of the disclosure can also be administered in a variety of unit dosage forms and their dosages will also vary with the size, potency, and in vivo half-life of the particular therapeutic being administered.

Doses of therapeutics of the disclosure will also vary depending on the manner of administration, the particular symptoms of the patient being treated, the overall health, condition, size, and age of the patient, and the judgment of the prescribing physician.

The formulations of the application can be distributed as articles of manufacture comprising packaging material and a pharmaceutical agent which comprises the antibody capable of inhibiting complement and a pharmaceutically acceptable carrier as appropriate to the mode of administration. The packaging material may include a label which indicates that the formulation is for use in the treatment of antibody mediated neuropathies. Although antibodies are preferred, especially anti-C5 antibodies which have already been shown to be safe and effective at decreasing the accumulation of downstream complement components in persons, the use of other complement inhibitors is also contemplated by this disclosure. The pharmaceutical formulations and uses of the disclosure may be combined with any known complement inhibitors or antibody mediated neuropathy treatments known in the art (supra).

Methods of Treatment

Methods of the application may be used to treat antibody mediated neuropathy associated symptoms. For example, methods of the application may be used to treat AGA mediated neuropathy symptoms. Methods of the application may be used to treat Guillain-Barré syndrome associated symptoms. Treatment of antibody mediated neuropathies may be administered by standard means. Treatments of the application may be used in combination with other treatments of the application or known treatments for antibody mediated neuropathies. Treatments of the application may be co-administered with other treatments that treat symptoms of antibody mediated neuropathies. Administration of the therapeutics of the disclosure will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody capable of inhibiting complement to be administered.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

The present methods are described with reference to the following Examples, which are offered by way of illustration and are not intended to limit the disclosure in any manner. Standard techniques well known in the art or the techniques specifically described below are utilized.

EXAMPLES

Example 1

Eculizumab Prevents Complement-Mediated Structural and Functional Lesions in the In Vitro MFS Model In the in vitro MFS model, treatment of diaphragm nerve-muscle preparations with CGM3 anti-GQ1b mAb and normal human serum (NHS), in the presence of an irrelevant isotype matched mAb (100 μg/ml), that served as a negative control for eculizumab, induced complement activation at NMJs. This was morphologically evidenced by C3c and MAC deposition (FIGS. 1A, 1B, 1D, 1E and 1F), as well as damaged perisynaptic Schwann cells (pSCs) and motor nerve terminals shown by ethidium homodimer-1 (EthD-1) staining and loss of neurofilament (NF) staining, respectively (FIGS. 1C, 1E and 1F). These features were identical to those reported before (Goodyear et al. *J. Clin. Invest* 104:697-708 (1999); Halstead et al. *Brain* 127:2109-2123 (2004); O'Hanlon et al. *Brain* 124:893-906 (2001)). The addition of 100 μg/ml eculizumab to the NHS as complement source completely prevented MAC deposition (FIGS. 1B, 1D, 1E and 1F; p<0.001) and terminal axonal NF loss (FIGS. 1C and 1F; p<0.001), while the deposition of the earlier complement component C3c was not affected (FIGS. 1A and 1D; p=0.2). Furthermore, damage to pSCs was abolished as only 2% of the 1439 NMJs investigated had one or more EthD-1 positive nuclei, compared with 33% of 1529 NMJs investigated in control mAb-treated tissue (FIG. 1E; p<0.001).

Figure 2:
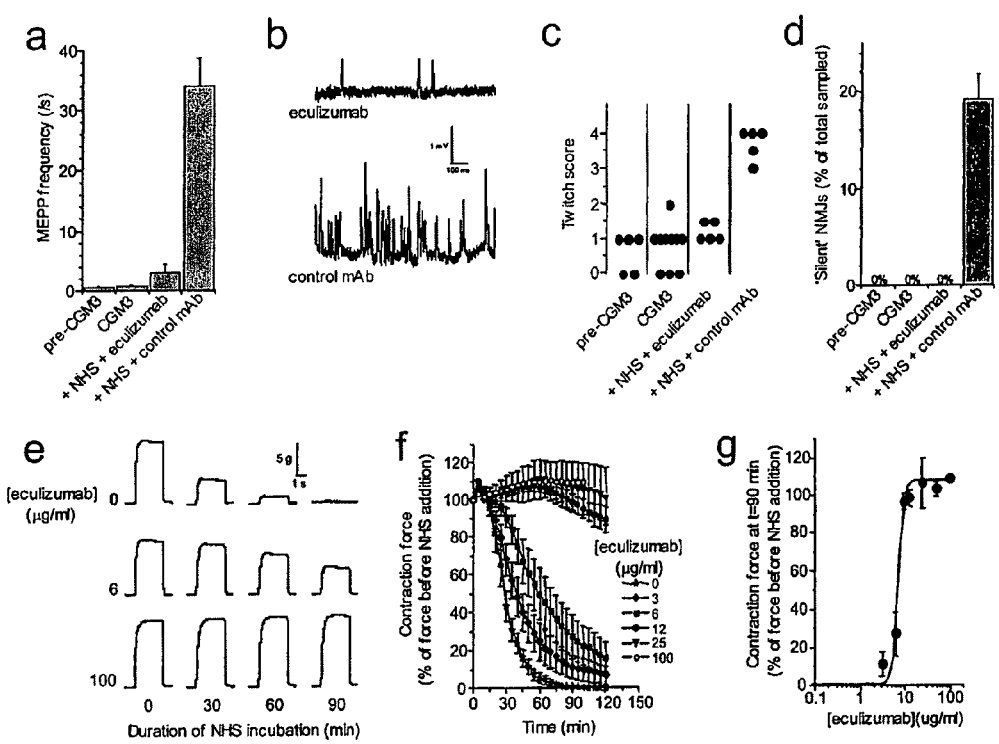
FIGS. 2A-2G show eculizumab protects against electrophysiological and functional defects induced at NMJs in the in vitro MFS model. Mouse hemi-diaphragm preparations were pre-incubated with anti-GQ1b ganglioside mAb CGM3 (50 μg/ml) and subsequently treated with 40% normal human serum (NHS) with either added 100 μg/ml eculizumab (anti-human C5 neutralizing mAb) or non-specific isotype-matched control mAb.

These immunohistological observations paralleled the electrophysiological and functional observations. At CGM3 pre-incubated NMJs, NHS (40%) in the presence of the control mAb induced a large increase in the frequency of miniature endplate potentials (MEPPs, the postsynaptic events arising from spontaneous release of single acetylcholine quanta from the presynaptic motor nerve terminal), as previously observed (Goodyear et al. *J. Clin. Invest* 104:697-708 (1999)). This effect was almost completely prevented by 100 μg/ml eculizumab. The MEPP frequency was about $0.7\ s^{-1}$ before and after 50 μg/ml CGM3 incubation and rose to $34.0\pm4.6\ s^{-1}$ in the presence of NHS with 100 μg/ml control mAb added. By contrast the MEPP frequency was only $3.1\pm1.3$ s$^{-1}$ in the presence of NHS with 100 µg/ml eculizumab added (FIGS. 2A and 2B; n=5 muscles; p<0.001).

Eculizumab did not alter the muscle fiber resting membrane potential or MEPP amplitude, rise- and decay times (data not shown). As described before (Goodyear et al. *J. Clin. Invest* 104:697-708 (1999); Plomp et al. Ann. Neurol. 45:189-199 (1999)), asynchronous twitching of individual muscle fiber occurs during NHS incubation (median visual score 4; n=5 muscles). Eculizumab prevented such high grade of twitching with only a median score of 1 being observed (FIG. 2C; n=5 muscles, p<0.01, Mann-Whitney test), which equals the low basal levels observed in the observation periods before and after CGM3 incubation.

The final result of anti-CGM3/complement-mediated presynaptic damage is block of synaptic transmission at the NMJ due to the inability to release acetylcholine (Goodyear et al. *J. Clin. Invest* 104:697-708 (1999)). Eculizumab completely prevented this effect. No 'silent' NMJs (i.e. absence of MEPPs and nerve-stimulation evoked muscle action potentials) were encountered, whereas in the control mAb condition $19\pm2.6\%$ of the total number of NMJs sampled were observed to be silenced (FIG. 2D; n=5 muscles). Furthermore, we quantified the protective effect of eculizumab on muscle paralysis in the in vitro MFS model. Eculizumab inhibited loss of nerve stimulation-induced contraction force of hemi-diaphragm preparations in a concentration dependent manner following 200 µg/ml CGM3 and 33% NHS treatment (FIGS. 2E and 2F). In the control experiments without eculizumab, NHS induced almost complete loss of contraction force within 90 min. Addition of 3 or 6 µg/ml eculizumab to the NHS slowed down the rate of contraction force loss considerably (50% loss was observed at 39 and 60 min, respectively, compared to 27 min in the control condition; FIG. 2F). Higher eculizumab concentrations of 9 and 12 µg/ml were almost completely protective (>90% of the initial contraction left after 90 min) while 25, 50 and 100 µg/ml completely prevented any CGM3/NHS-induced loss of contraction. A Boltzmann sigmoidal curve fitted through the obtained concentration-effect data points yielded an $EC_{50}$ of 7.1 µg/ml for eculizumab under these conditions (FIG. 2G).

These immunohistological and functional analyses show that eculizumab efficiently prevents complement-mediated pathophysiological effects in the in vitro MFS model.

Example 2

Eculizumab Dose Response Curve In Vivo

Next the in vivo benefits of eculizumab in this murine model of Guillain-Barré syndrome were examined. Mice were passively immunized with anti-ganglioside antibody or PBS (as a negative control) followed by concomitant injections of NHS (intraperitoneal) and eculizumab (intravenous) at 0, 50, 100, 200, and 400 µg/mouse in PBS. Complement C3 was richly deposited at the NMJ of all mice receiving anti-ganglioside antibody. An increasing dose of eculizumab results in a dose-dependent reduction in MAC deposition at the NMJ (FIG. 3A). Examination of the neurofilament signal demonstrates preservation of axonal integrity at all doses of eculizumab investigated when compared to PBS treated baseline control. (n=3 for each dose) (FIG. 3B).

Example 3

Figure 4:
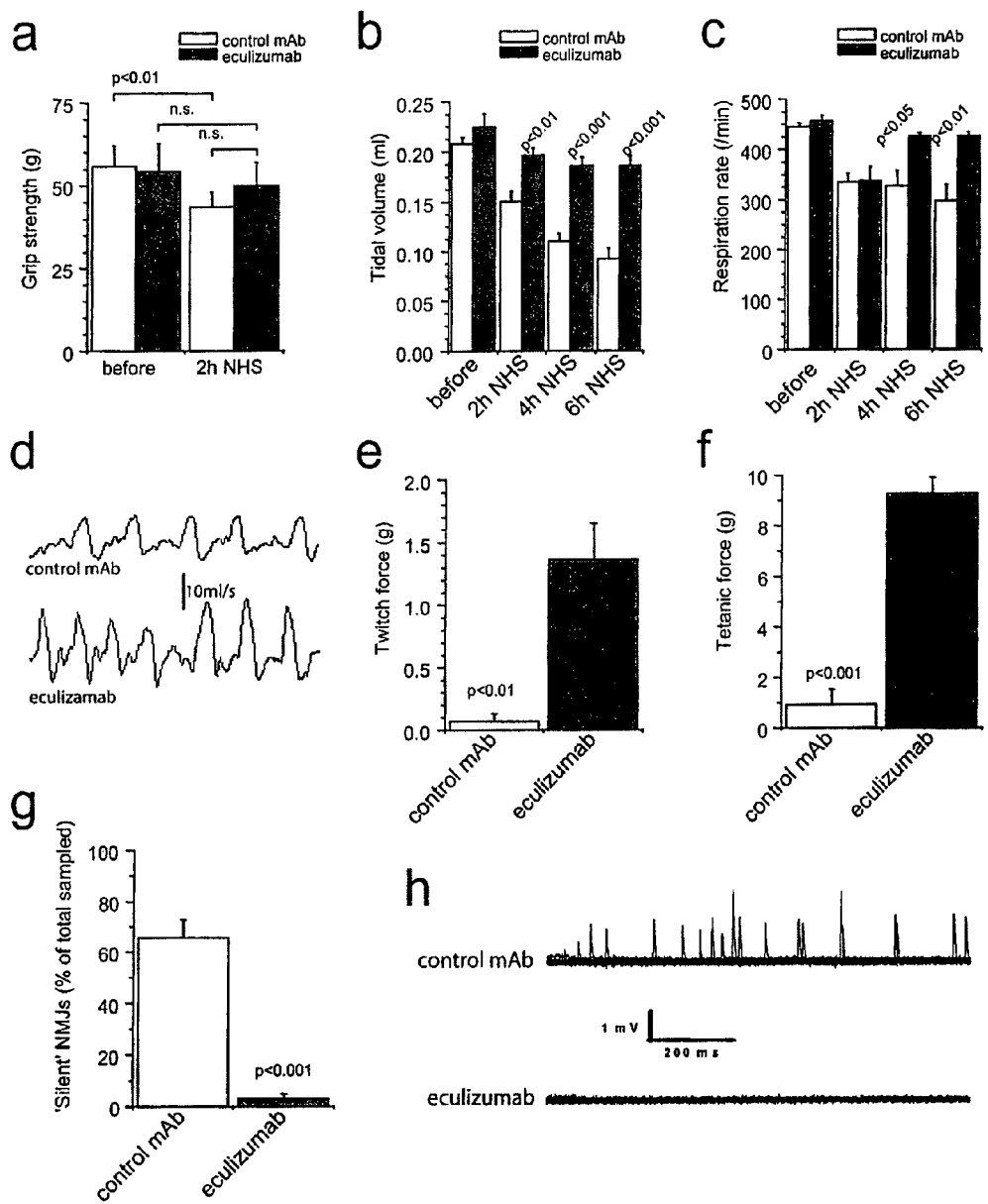

Eculizumab Protects Against Neuropathy and Respiratory Paralysis in an In Vivo MFS Model In order to determine the in vivo efficacy of eculizumab, we generated an in vivo MFS mouse model through intraperitoneal injection of CGM3 anti-GQ1b antibody and NHS as complement source. At 16 h after the CGM3 injection, a dose of 200 µg eculizumab or control mAb was administered systemically, via the tail vein, followed by intraperitoneal injection of 0.5 ml NHS). The protocol of different injection routes of eculizumab and NHS was applied to avoid the immediate inhibition of C5 in the NHS by eculizumab within the confinement of the peritoneal cavity. Mice treated with CGM3, NHS and control mAb (n=10) developed a general weak appearance, in some cases a low-back posture, invaginated abdominal flanks and breathing difficulties (panting) within 2 h following the NHS injection. Intravenous eculizumab injection completely prevented the development of these symptoms (n=11). We quantified weakness with grip-strength measurement in CGM3 pre-treated mice, before and 2 h after injection of control mAb or eculizumab and NHS (FIG. 4A). Control group mice (n=5) pulled $56.0\pm5.7$ g just before the control mAb and NHS injection, while the eculizumab group mice (n=5) pulled $543\pm8.4$ g (p=0.87) at this stage. The pulling force 2 h after control mAb/NHS injection was 22% lower ($43.7\pm4.5$ g; p<0.005). Eculizumab ameliorated such an effect (8% reduction; p=0.07). Respiratory disturbance was assessed with whole-body plethysmography continuously after mAb/NHS injection for a period of 6 h (FIGS. 4B and 4C; n=5 mice per group). The tidal volume before CGM3 injection was similar in both groups ($0.21\pm0.01$ and $0.22\pm0.03$ ml in the control mAb and eculizumab group, respectively). A reduction of approximately 50% (p<0.001) was observed in the control mAb group at 4 and 6 h after NHS injection. Such a decrease was largely prevented by eculizumab (only 17% reduction at these time points, FIG. 4B). Similarly, respiration rate was depressed in the control mAb group by approximately 30% (p<0.01) at 4 and 6 h post-NHS injection. In the eculizumab group, this reduction was only 7% (FIG. 4C). Both treatment groups showed an equal initial reduction of about 40% of the respiration rate when measured 2 h post mAb/NHS, compared to the rate before CGM3 injection, which apparently was due to the intraperitoneal injection regimen. Example traces of the respiration signals obtained are shown in FIG. 4D.

Figure 5:
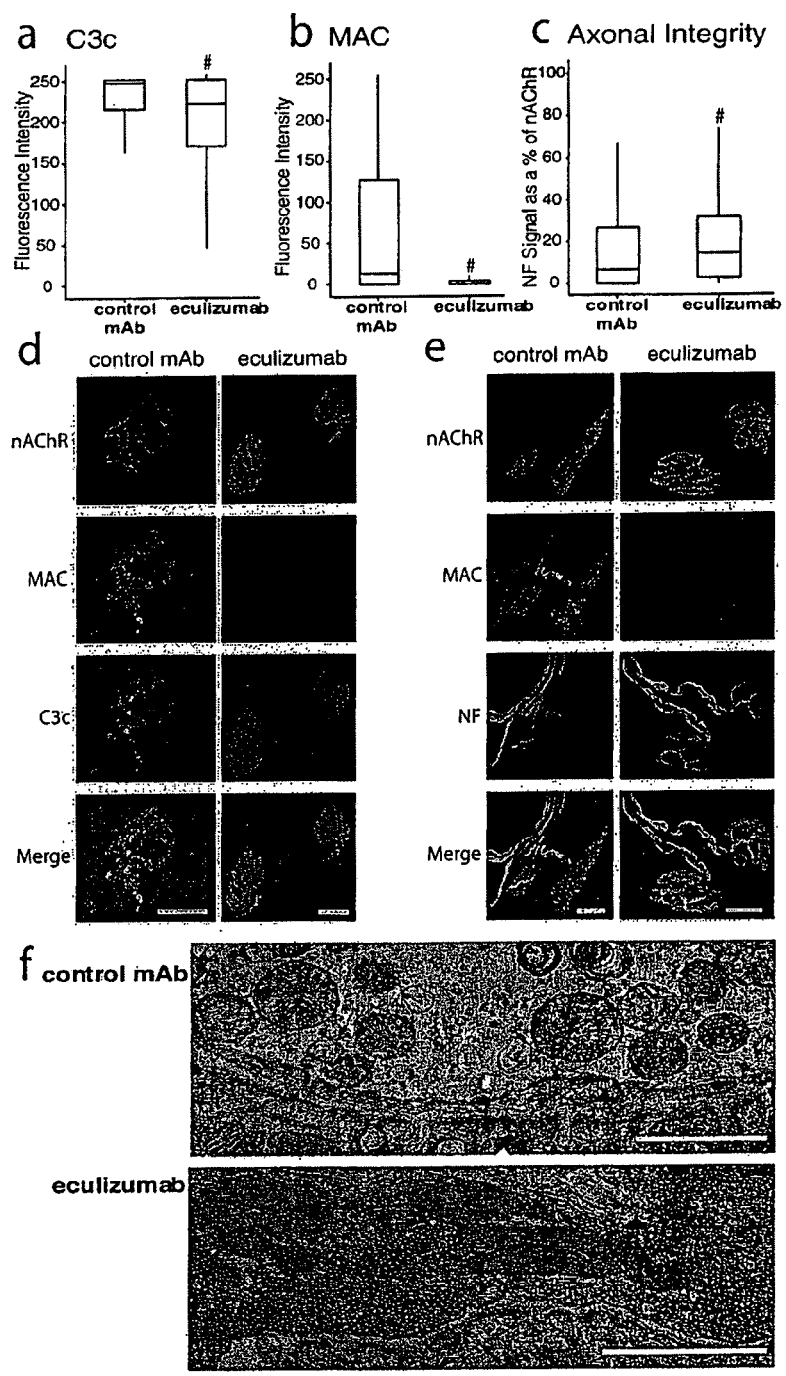
FIGS. 5A-5F show a morphological analysis of NMJs of diaphragm tissue from in vivo MFS mice. Mice were passively immunized with 1.5 mg anti-GQ1b ganglioside mAb, CGM3, followed 16 h later with concomitant injections of 0.5 ml 100% normal human serum (intraperitoneal) and eculizumab or control mAb (intravenous; 200 μg).

The hemi-diaphragm phrenic nerve preparations were dissected from in vivo CGM3/NHS treated mice at 4 h following NHS injection and performed electrophysiological measurements at NUN, muscle contraction experiments, and detailed immunohistological analyses. Visual inspection indicated that only a very small part of the muscles from control mAb-treated mice contracted upon supramaximal electrical stimulation of the phrenic nerve, as compared to a complete contraction of muscles obtained from eculizumab-treated mice. In in vitro contraction experiments in tissues harvested from passive immunizations, this effect was quantified (FIGS. 4E and 4F). Twitch and tetanic (40 Hz) tension were $0.07\pm0.06$ and $0.92\pm0.61$ g, respectively, in the control mAb group (n=4), while in the eculizumab group (n=4) these were $1.36\pm0.29$ and $9.26\pm0.65$ g, respectively, equalling the values of muscles from non-NHS treated age-matched mice (data not shown). With electrophysiological analysis we tested whether paralysis was caused by NMJ dysfunction. In dissected muscles from the control mAb group $66\pm7\%$ of the sampled NMJs had been 'silenced', i.e. there were no detectable MEPPs and no muscle action potentials upon nerve stimulations. In the eculizumab group only $3\pm2\%$ had been 'silenced' (FIGS. 4G and 4H; p<0.001). Immunohistological analysis showed that CGM3 was deposited equally at NMJs of the two treatment groups (data not shown). C3c deposits were identified at NMJs of both groups, albeit with a somewhat less intensity in the eculizumab group (FIGS. 5A and 5D; p<0.001). MAC was clearly deposited at NMJs of muscles from control mAb-treated mice but virtually absent in the eculizumab-treated group (FIGS. 5B, 5D and 5E). Eculizumab prevented loss of terminal integrity at NMJs of control-mAb-treated mice, as evidenced by the NF signal intensity and pattern overlying the endplate region, i.e. terminal axonal branching clearly remaining intact (FIGS. 5C and 5E). In addition, electron microscopy showed the presence of a well-preserved presynaptic ultrastructure at the NMJ of eculizumab-treated mice in comparison with that of control-mAb-treated mice which showed characteristic terminal swelling, synaptic vesicle depletion and swollen mitochondria (FIG. 5F) (O'Hanlon et al. *Brain* 124:893-906 (2001)). These electrophysiological, functional and immunohistological data show that complement-mediated terminal motor neuropathy occurs in our in vivo MFS model and that diaphragm paralysis contributes to the observed respiratory deficits. Most importantly, in vivo eculizumab treatment effectively prevented these in vivo neuropathological defects.

Example 4

Methods

Mice

Male Balb/c mice (3-6 weeks old, 10-25 g) were obtained from Harlan (UK or NL). In some muscle contraction experiments (see below) male and female GM2/GD2-synthase null-mutant mice (Bullens et al. *J. Neurosci.* 22:6876-6884 (2002)) were used at 12-22 weeks of age (19-37 g). All animal experiments were carried out in accordance to UK Home Office guidelines (UK PPL60/3096), Dutch law and Glasgow and Leiden University guidelines.

Monoclonal Antibodies and Normal Human Serum

The IgM anti-GQ1b ganglioside mAb, CGM3 was derived from mice inoculated with a GT1a-bearing *Campylobacter jejuni* lipooligosaccharide (Goodyear et al. *J. Clin. Invest* 104:697-708 (1999)). CGM3 reacts with gangliosides GQ1b, GD3 and GT1a that all share the terminal disialylgalactose structure. Previous studies have shown that CGM3 has similar ganglioside specificity and induced identical complement-dependent pathogenic effects as human MFS sera (Goodyear et al. *J. Clin. Invest* 104:697-708 (1999)). CGM3 concentration was measured using quantitative ELISA (Bethyl Laboratories, Texas, USA). Normal human serum (NHS) was taken from a single donor stock that had been freshly frozen and stored in multiple aliquots at −70° C. to preserve complement activity. Prior to experimental use, CGM3 and NHS were dialyzed for 24 h at 4° C. against Ringer's solution (116 mM NaCl, 4.5 mM KCl, 1 mM $MgCl_2$, 2 mM $CaCl_2$, 1 mM $NaH_2PO_4$, 23 mM $NaHCO_3$, 11 mM glucose, pH 7.4), pre-gassed with 95% $O_2$/5% $CO_2$. The humanized anti-human C5 mAb eculizumab and a non-specific isotype-matched control mAb ALXN3300 were obtained from Alexion Pharmaceuticals (Cheshire, USA) and stored at 4° C.

In Vitro MFS Model

The in vitro model for MFS using CGM3 and NHS has been described before (Goodyear et al. *J. Clin. Invest* 104: 697-708 (1999); O'Hanlon et al. *Brain* 124:893-906 (2001)). In short, mouse hemi-diaphragms with phrenic nerve attached (or triangularis sterni muscle in some cases for illustrative NMJ immunohistology) were dissected and mounted in Ringer's medium at room temperature (20-22° C.). Untreated small control sections were removed from each muscle preparation prior to any incubations and snap frozen on dry ice for subsequent baseline immunohistological analysis. Muscles were incubated with CGM3 (50 µg/ml) for 2-2.5 h at 32° C., then for 30 min at 4° C. and then equilibrated for 10 mins at room temperature, rinsed in Ringer's medium and subsequently exposed to 33 or 40% NHS in Ringer's medium for 1 h at room temperature. Eculizumab (100 µg/ml) or the control mAb (100 µg/ml) was mixed with NHS 10 min prior to the incubation of the muscle preparation. In vitro electrophysiological measurements at the NMJ (see below) and scoring of muscle fiber twitchings, a hallmark of uncontrolled transmitter release at NMJs in this model (Jacobs et al. *Muscle Nerve* 25:549-558 (2002); O'Hanlon et al. *Brain* 124: 893-906 (2001)), were performed before and after CGM3 incubation, and during the 1 h NHS incubation. Muscle strips were frozen on dry ice and stored at −20° C., both before and after incubation with NHS. NMJs and terminal motor axons were assessed for levels of IgM, C3c, MAC, NF and for pSC viability (see below).

In Vivo MFS Model

Balb/c mice (3-4 weeks old, 10-15 g) were injected intraperitoneally with 1.5 mg CGM3, followed 16 h later by an intraperitoneal injection of 0.5 ml 100% NHS. Mice were observed for a further 4-6 h and analyzed with whole-body plethysmography (see below) and grip-strength testing as described before (Kaja et al. *Eur J. Neurosci* 25:2009-2020 (2007)). The mice were then killed by $CO_2$ asphyxiation and hemi-diaphragm muscle tissue was dissected and analyzed in electrophysiological and muscle contraction experiments (see below) or further processed for immunohistological analyses (see below). The effect of eculizumab on the in vivo symptoms and the subsequently analyzed electrophysiological, functional and histological lesions was tested in this model by injecting 200 µg eculizumab or control mAb in the tail vein, shortly before intraperitoneal NHS injection. Initial dose-range finding experiments (data not shown) indicated that eculizumab at doses of >50 µg/mouse protected against neuropathy.

Plethysmography

Non-invasive whole-body plethysmography (EMMS, Hants, UK) was employed to demonstrate changes in breathing parameters in in vivo experiments. Baseline data were collected prior to onset of experiment. Mice were injected with CGM3 followed by NHS with eculizumab or control mAb 16 h later (protocol as above) and monitored continuously for 6 h. Flow derived parameters of breath frequency and tidal volume were collected from 25 accepted breaths and averaged over 1 h periods.

In Vitro Electrophysiological Analysis of NMJs and Visual Scoring of Muscle Contractility Left and right hemi-diaphragms with their phrenic nerve attached were dissected and pinned out in a silicone rubber-lined dish in 1.5 ml Ringer's medium at room temperature. Intracellular recordings of miniature endplate potentials (MEPPs, the postsynaptic events arising from spontaneous release of single acetylcholine quanta from the presynaptic motor nerve terminal) were made at NMJs at 20-22° C. Muscle fibers were impaled near the NMJ with a 10-20 MΩ glass micro-electrode filled with 3 M KCl, connected to a GeneClamp 500B amplifier (Axon Instruments/Molecular Devices, Union City, Calif., USA) for amplifying and filtering (10 kHz low-pass) of the signal. Signals were digitized, stored and analyzed (off-line) using a Digidata 1322A interface, Clampex 9.2 and Clampfit 9.2 programs (all from Axon Instruments/Molecular Devices), Mini Analysis 6.0 (Synaptosoft, Fort Lee, USA) and routines programmed in Matlab (The MathWorks Inc., Natick, Mass., USA).

The occurrence of spontaneous asynchronous fiber twitches that are induced by a high MEPP frequency resulting from CGM3/complement-mediated presynaptic damage (Plomp et al. *Ann. Neurol.* 45:189-199 (1999)) was scored visually every 5 min (O'Hanlon et al. *Brain* 124:893-906 (2001)). The tissue scored 0 for no activity, 1 for the twitching of <10 fibers, 2 for a small amount of twitching across the tissue, 3 for a moderate amount and 4 for an extensive amount. The average score during each measuring period was calculated. The final result of CGM3/complement-mediated presynaptic damage is a silencing of synaptic transmission at the NMJ. The number of 'silent' NMJs (i.e. without detectable MEPPs and occurrence of phrenic nerve-stimulation evoked muscle action potentials) was expressed as percentage of the total number of NMJs sampled (8-41) in a muscle under each experimental condition.

Muscle Contraction Experiments

The protective efficacy of eculizumab on in vitro CGM3/NHS-induced loss of nerve stimulation-evoked contraction force of the hemi-diaphragm preparation was tested. We used diaphragm from GM2/GD2-synthase null-mutant mice because earlier studies showed a somewhat higher sensitivity of muscle of this strain to CGM3/NHS-induced loss of contraction (Bullens et al. *J. Neurosci.* 22:6876-6884 (2002)). Left and right phrenic nerve/hemi-diaphragm preparations that had been pre-incubated with 200 µg/ml CGM3 for 3 h at 32° C. were mounted in a silicone-rubber lined dish containing 2.25 ml Ringer's medium at room temperature (20-22° C.), continuously bubbled with 95% $O_2$/5% $CO_2$. The ribcage side of the muscle was thoroughly fixed to the bottom of the dish by multiple small pins and the central tendon was connected via a metal hook and a string to a force transducer that was connected to an amplifier and digitizing equipment, as described earlier (Kaja et al. *Eur J. Neurosci* 25:2009-2020 (2007)). Supramaximal stimuli (usually ~10 V) of 100 µs duration were delivered every 5 min for 3 s at 40 Hz from a Master-8 programmable stimulator (AMPI, Jerusalem, Israel). Basic tension was adjusted with a vernier control to obtain maximal stimulated tetanic contraction force (usually about 10 g). Stability of the elicited contraction was monitored for 30-50 min. Subsequently, the medium was replaced by NHS (33%) to which eculizumab (3, 6, 9, 12, 25, 50 or 100 µg/ml) had been added and admixed for ~10 min prior to addition and the effect was monitored for 100-200 min, under continuous gentle bubbling with 95% $O_2$/5% $CO_2$. In the control experiments without added eculizumab, 100 µg/ml of the control mAb was added to the NHS. The amplitude of contractions was cursor-measured off-line in the Clampfit 9.0 program (Axon Instruments/Molecular Devices, Union City, USA), at 2 s after the start of each nerve stimulation train.

Tetanic and twitch contraction forces were also measured upon in vitro nerve stimulation of left hemi-diaphragm muscles that were dissected from mice that had been subjected to the in vivo MFS protocol.

Immunohistological Analyses

Unfixed hemi-diaphragm sections were mounted in Lipshaw's M-1 mounting medium (Pittsburgh, Pa., USA), and longitudinal cryostat sections (8-20 µm) were cut onto 3-aminopropyltriethoxysilane coated slides, air-dried, then stored at −20° C. To localize NMJs, TRITC and bodipy-labelled α-bungarotoxin (α-BTx, diluted 1/750 to 1.3 µg/ml; Molecular Probes, Eugene, Oreg.) were used. The intermediate complement component C3c was detected by incubation with FITC-labelled rabbit anti-C3c (1/300; Dako, Ely, UK) for 1 h at 4° C. MAC was detected using mouse anti-human C5b-9 (1/50; Dako) followed by FITC conjugated goat anti-mouse IgG (1/300), both for 1 h at 4° C.

For NF staining, sections of unfixed tissue were pre-incubated for 1 h at 4° C. with TRITC-conjugated α-BTx, rinsed, immersed in ethanol at −20° C. for 20 min, then incubated overnight at room temperature with the rabbit polyclonal serum 1211 (1/750; reactive with phosphorylated NF; Affiniti Research Products Ltd. Exeter, UK) followed by FITC conjugated goat anti-rabbit IgG (1/300; Southern Biotechnology Associates) for 3 h at 4° C. All detection antibodies were diluted in phosphate-buffered saline (PBS).

pSC viability was assessed using EthD-1, a membrane impermeant dye that labels with red fluorescence the nucleic acids of membrane-permeabilized cells (Molecular Probes, Eugene, Oreg., USA). In brief, nerve-muscle preparations were exposed to Ringer's containing 2 µM EthD-1. The tissue was incubated in the dark at room temperature for 1 h, rinsed in Ringer's solution and frozen for immunohistology. NMJs were identified in 15 µm cryostat sections by staining with bodipy conjugated α-BTx (1.3 µg/ml), and the percentage of NMJs with EthD-1 positive nuclei at NMJs was calculated.

For illustrations, whole mount triangularis sterni muscles were incubated with CGM3 (50 µg/ml) and fluorochrome-conjugated α-BTx (TRITC/FITC/CY5) (2 µg/ml; 1:500), followed by NHS plus eculizumab or control mAb. Preparations were incubated with fluorescently conjugated α-BTx and various combinations of the following: mouse anti-C5b-9 (1:40; Dako), anti-C3c-FITC (1:200; Dako), or EthD-1 (2 µM) in Ringer's medium for 1 h at room temperature, rinsed in Ringer's medium, followed by fixation for 20 min in 4% formaldehyde in PBS. Unreactive aldehyde groups were quenched, by incubating with 0.1 M glycine for 10 min. The antibodies were then reapplied in PBS and agitated overnight at room temperature. For staining of intracellular antigens, muscle was fixed in 4% formaldehyde for 20 min followed by 10 min in 0.1M glycine and then incubated in a permeabilizing solution of 0.5% Triton-X100 in PBS for 30 min at RT, and either rabbit anti-S100 (1:150; Dako) or rabbit anti-NF (1:150; Chemicon, Hampshire, UK) diluted in permeabilizing solution applied overnight at room temperature. Tissue was rinsed in PBS and where necessary incubated in the following fluorescently conjugated antibodies diluted 1:300; anti-rabbit IgG-FITC, anti-mouse IgG-FITC or -TRITC and agitated for 7 h at RT in the dark. Tissue was rinsed in PBS and mounted in Citifluor mounting medium (Citifluor Products, Canterbury, UK).

Image Acquisition, Quantitation and Statistical Analysis

Digital images were captured using both Zeiss Pascal confocal laser scanning microscope and Zeiss Axio Imager Z1 with ApoTome. Image-analysis measurements were made using Scion Image (Scion Corporation, Frederick, Md., USA) image analysis software. For quantitative analysis of IgM, C3c, MAC and NF, 3 staining runs of each marker were performed on tissue from at least 3 individual hemi-diaphragms, and quantified as previously described (O'Hanlon et al. *Brain* 124:893-906 (2001)). All studies were observer blinded. For immunohistological analysis of non-parametric data, statistical comparisons were made using Mann-Whitney Test employing a 1% level of significance. For comparison of EthD-1 positive pSC at the NMJ, chi-squared test was used at 1% level of significance.

REFERENCES

1. Fisher, M. 1956. An unusual variant of acute idiopathic polyneuritis (syndrome of opthalmoplegia, ataxia and areflexia). *N.Engl.J.Med.* 255:57-65.
2. Hughes, R. A. and Cornblath, D. R. 2005. Guillain-Barre syndrome. *Lancet* 366:1653-1666.
3. Bowes, T., Wagner, E. R., Boffey, J., Nicholl, D., Cochrane, L., Benboubetra, M., Conner, J., Furukawa, K., Furukawa, K., and Willison, H. J. 2002. Tolerance to self gangliosides is the major factor restricting the antibody response to lipopolysaccharide core oligosaccharides in *Campylobacter jejuni* strains associated with Guillain-Barre syndrome. *Infect.Immun.* 70:5008-5018.
4. Goodyear, C. S., O'Hanlon, G. M., Plomp, J. J., Wagner, E. R., Morrison, I., Veitch, J., Cochrane, L., Bullens, R. W., Molenaar, P. C., Conner, J. et al. 1999. Monoclonal antibodies raised against Guillain-Barre syndrome-associated *Campylobacter jejuni* lipopolysaccharides react with neuronal gangliosides and paralyze muscle-nerve preparations. *J.Clin.Invest* 104:697-708.
5. Yuki, N. 2001. Infectious origins of, and molecular mimicry in, Guillain-Barre and Fisher syndromes. *Lancet Infect.Dis.* 1:29-37.
6. Willison, H. J. and O'Hanlon, G. M. 1999. The immunopathogenesis of Miller Fisher syndrome. *J. Neuroimmunol.* 100:3-12.
7. Ledeen, R. W. 1985. Gangliosides of the neuron. *Trends in Neurosciences* 8:169-174.
8. Chiba, A., Kusunoki, S., Obata, H., Machinami, R., and Kanazawa, I. 1993. Serum anti-GQ1b IgG antibody is associated with opthalmoplegia in Miller Fisher syndrome and Guillain-Barre syndrome: clinical and immunohistochemical studies. *Neurology* 43:1911-1917.
9. Buchwald, B., Weishaupt, A., Toyka, K. V., and Dudel, J. 1995. Immunoglobulin G from a patient with Miller-Fisher syndrome rapidly and reversibly depresses evoked quantal release at the neuromuscular junction of mice. *Neurosci. .Lett.* 201:163-166.
10. Plomp, J. J., Molenaar, P. C., O'Hanlon, G. M., Jacobs, B. C., Veitch, J., Daha, M. R., Van Doorn, P. A., Van der Meche, F. G. A., Vincent, A., Morgan, B. P. et al. 1999. Miller Fisher anti-GQ1b antibodies: a-latrotoxin-like effects on motor end plates. *Ann.Neurol.* 45:189-199.
11. Roberts, M., Willison, H., Vincent, A., and Newsom-Davis, J. 1994. Serum factor in Miller-Fisher variant of Guillain-Barre syndrome and neurotransmitter release. *Lancet* 343:454-455.
12. Schwarz, A. and Futerman, A. H. 1996. The localization of gangliosides in neurons of the central nervous system: The use of anti-ganglioside antibodies. Biochimica et *Biophysica Acta—Reviews on Biomembranes* 1286:247-267.
13. Lange, D. J., Deangelis, T., and Sivak, M. A. 2006. Single-fiber electromyography shows terminal axon dysfunction in Miller Fisher syndrome: a case report. *Muscle Nerve* 34:232-234.
14. Lo, Y. L., Leoh, T. H., Dan, Y. F., Lim, L. L., Seah, A., Fook-Chong, S., and Ratnagopal, P. 2006. Presynaptic neuromuscular transmission defect in the Miller Fisher syndrome. *Neurology* 66:148-149.
15. Sartucci, F., Cafforio, G., Borghetti, D., Domenici, L., Orlandi, G., and Murri, L. 2005. Electrophysiological evidence by single fibre electromyography of neuromuscular transmission impairment in a case of Miller Fisher syndrome. *Neurol.Sci.* 26:125-128.
16. Uncini, A. and Lugaresi, A. 1999. Fisher syndrome with tetraparesis and antibody to GQ1b: evidence for motor nerve terminal block. *Muscle Nerve* 22:640-644.
17. Wirguin, I., Ifergane, G., Almog, Y., Lieberman, D., Bersudsky, M., and Herishanu, Y. O. 2002. Presynaptic neuromuscular transmission block in Guillain-Barre syndrome associated with anti-GQ1b antibodies. *Neuromuscul.Disord.* 12:292-293.
18. Bullens, R. W., O'Hanlon, G. M., Goodyear, C. S., Molenaar, P. C., Conner, J., Willison, H. J., and Plomp, J. J. 2000. Anti-GQ1b antibodies and evoked acetylcholine release at mouse motor endplates. *Muscle Nerve* 23:1035-1043.
19. Halstead, S. K., O'Hanlon, G. M., Humphreys, P. D., Morrison, D. B., Morgan, B. P., Todd, A. J., Plomp, J. J., and Willison, H. J. 2004. Anti-disialoside antibodies kill perisynaptic Schwann cells and damage motor nerve terminals via membrane attack complex in a murine model of neuropathy. *Brain* 127:2109-2123.
20. Jacobs, B. C., Bullens, R. W., O'Hanlon, G. M., Ang, C. W., Willison, H. J., and Plomp, J. J. 2002. Detection and prevalence of alpha-latrotoxin-like effects of serum from patients with Guillain-Barre syndrome. *Muscle Nerve* 25:549-558.
21. O'Hanlon, G. M., Plomp, J. J., Chakrabarti, M., Morrison, I., Wagner, E. R., Goodyear, C. S., Yin, X., Trapp, B. D., Conner, J., Molenaar, P. C. et al. 2001. Anti-GQ1b ganglioside antibodies mediate complement-dependent destruction of the motor nerve terminal. *Brain* 124:893-906.
22. Hafer-Macko, C. E., Sheikh, K. A., Li, C. Y., Ho, T. W., Cornblath, D. R., McKhann, G. M., Asbury, A. K., and Griffin, J. W. 1996. Immune attack on the Schwann cell surface in acute inflammatory demyelinating polyneuropathy. *Ann.Neurol.* 39:625-635.
23. Hartung, H. P., Schwenke, C., Bitter-Suermann, D., and Toyka, K. V. 1987. Guillain-Barre syndrome: activated complement components C3a and C5a in CSF. *Neurology* 37:1006-1009.
24. Koski, C. L., Sanders, M. E., Swoveland, P. T., Lawley, T. J., Shin, M. L., Frank, M. M., and Joiner, K. A. 1987. Activation of terminal components of complement in patients with Guillain-Barre syndrome and other demyelinating neuropathies. *J.Clin.Invest* 80:1492-1497.
25. Sanders, M. E., Koski, C. L., Robbins, D., Shin, M. L., Frank, M. M., and Joiner, K. A. 1986. Activated terminal complement in cerebrospinal fluid in Guillain-Barre syndrome and multiple sclerosis. *J.Immunol.* 136:4456-4459.
26. Halstead, S. K., Humphreys, P. D., Goodfellow, J. A., Wagner, E. R., Smith, R. A., and Willison, H. J. 2005. Complement inhibition abrogates nerve terminal injury in Miller Fisher syndrome. *Ann.Neurol.* 58:203-210.
27. Thomas, T. C., Rollins, S. A., Rother, R. P., Giannoni, M. A., Hartman, S. L., Elliott, E. A., Nye, S. H., Matis, L. A., Squinto, S. P., and Evans, M. J. 1996. Inhibition of complement activity by humanized anti-05 antibody and single-chain Fv. *Mol.Immunol.* 33:1389-1401.
28. Ramaglia, V., King, R. H., Nourallah, M., Wolterman, R., de Jonge, R., Ramkema, M., Vigar, M. A., van der, W. S., Morgan, B. P., Troost, D. et al. 2007. The membrane attack complex of the complement system is essential for rapid Wallerian degeneration. *Neurosci.* 27:7663-7672.
29. Hillmen, P., Young, N. S., Schubert, J., Brodsky, R. A., Socie, G., Muus, P., Roth, A., Szer, J., Elebute, M. O., Nakamura, R. et al. 2006. The complement inhibitor eculizumab in paroxysmal nocturnal hemoglobinuria. *N.Engl. .J.Med.* 355:1233-1243.
30. Morgan, B. P. 1989. Mechanisms of tissue damage by the membrane attack complex of complement. *Complement Inflamm.* 6:104-111.
31. Susuki, K., Rasband, M. N., Tohyama, K., Koibuchi, K., Okamoto, S., Funakoshi, K., Hirata, K., Baba, H., and Yuki, N. 2007. Anti-GM1 antibodies cause complement-mediated disruption of sodium channel clusters in peripheral motor nerve fibers. *J.Neurosci.* 27:3956-3967.
32. Putzu, G. A., Figarella-Branger, D., Bouvier-Labit, C., Liprandi, A., Bianco, N., and Pellissier, J. F. 2000. Immunohistochemical localization of cytokines, C5b-9 and ICAM-1 in peripheral nerve of Guillain-Barre syndrome. *J.Neurol.Sci.* 174:16-21.
33. Hill, A., Richards, S. J., and Hillmen, P. 2007. Recent developments in the understanding and management of paroxysmal nocturnal haemoglobinuria. *Br.J.Haematol.* 137:181-192.
34. van Koningsveld, R., Steyerberg, E. W., Hughes, R. A., Swan, A. V., Van Doorn, P. A., and Jacobs, B. C. 2007. A clinical prognostic scoring system for Guillain-Barre syndrome. *Lancet Neurol.* 6:589-594.
35. Morgan, B. P., Chamberlain-Banoub, J., Neal, J. W., Song, W., Mizuno, M., and Harris, C. L. 2006. The membrane attack pathway of complement drives pathology in passively induced experimental autoimmune myasthenia gravis in mice. *Clin.Exp.Immunol.* 146:294-302.
36. Rice, C. E. 1950. The interchangeability of the complement components of different animal species; literature survey. *Can.J.Comp Med.Vet.Sci.* 14:369-379.
37. Bullens, R. W., O'Hanlon, G. M., Wagner, E., Molenaar, P. C., Furukawa, K., Furukawa, K., Plomp, J. J., and Willison, H. J. 2002. Complex gangliosides at the neuromuscular junction are membrane receptors for autoantibodies and botulinum neurotoxin but redundant for normal synaptic function. *J.Neurosci.* 22:6876-6884.
38. Kaja, S., van de Ven, R. C., van Dijk, J. G., Verschuuren, J. J., Arahata, K., Frants, R. R., Ferrari, M. D., van den Maagdenberg, A. M., and Plomp, J. J. 2007. Severely impaired neuromuscular synaptic transmission causes muscle weakness in the Cacna1a-mutant mouse rolling Nagoya. *Eur J.Neurosci* 25:2009-2020.

What is claimed is:

1. A method of treating a mammal having Guillain-Barré syndrome, said method comprising administering to the mammal a therapeutically effective amount of a complement cascade inhibitor, wherein said inhibitor is an antibody or antigen-binding fragment thereof which specifically binds: (i) to complement component C5 and inhibits the cleavage of C5 into fragments C5a and C5b; and/or (ii) to C5b, wherein said antibody or antigen-binding fragment thereof inhibits membrane attack complex (MAC) formation.

2. The method of claim 1 wherein said mammal has the Miller Fisher variant of Guillain-Barré syndrome.

3. The method of claim 1 wherein said mammal is a human.

4. The method of claim 1 wherein said antibody or antigen-binding fragment thereof is at least one selected from the group consisting of: a polyclonal antibody, a monoclonal antibody or antigen-binding fragment thereof, a diabody, a chimerized or chimeric antibody or antigen-binding fragment thereof, a humanized antibody or antigen-binding fragment thereof, a deimmunized antibody or antigen-binding fragment thereof, a fully human antibody or antigen-binding fragment thereof, a single chain antibody, an Fv, an Fab, an Fab', and an $F(ab')_2$.

5. The method of claim 1 wherein said antibody is eculizumab.

6. The method of claim 1 wherein said antigen-binding fragment thereof is pexelizumab.

7. The method of claim 5 wherein said treating is chronic.

8. The method of claim 6 wherein said treating comprises treating an acute episode.

9. The method of claim 1 wherein said antibody or antigen-binding fragment thereof is formulated to be administrable to said mammal intravenously.

10. The method of claim 1 wherein said antibody or antigen-binding fragment thereof is formulated to be administrable to said mammal systemically.

11. The method of claim 1, wherein said antibody or antigen-binding fragment thereof is formulated to be administrable to said mammal locally.

12. The method of claim 1 wherein said treating results in decreased neural injury in said mammal.

13. The method of claim 1 wherein said treating results in decreased membrane attack complex (MAC) formation at presynaptic neuromuscular junctions.

14. The method of claim 1 wherein said treating restores a normal frequency of miniature endplate potentials.

15. The method of claim 1 wherein said treating restores synaptic transmission at the neuromuscular junctions.

16. The method of claim 1 wherein said treating inhibits loss of terminal integrity at the neuromuscular junctions.

* * * * *